United States Patent [19]
Bourinbaiar

[11] Patent Number: 5,811,390
[45] Date of Patent: Sep. 22, 1998

[54] USE OF BETA HCG FOR THE CONTROL OF RETROVIRAL INFECTION

[75] Inventor: Aldar S. Bourinbaiar, New York, N.Y.

[73] Assignee: Metatron, Inc., Deer Park, N.Y.

[21] Appl. No.: 517,755

[22] Filed: Aug. 22, 1995

[51] Int. Cl.$^6$ .......................... A61K 38/16; C07K 14/59
[52] U.S. Cl. ............................................ 514/8; 530/398
[58] Field of Search .................................. 530/398; 514/8

[56] References Cited

U.S. PATENT DOCUMENTS

| 4,271,069 | 6/1981 | Tsong et al. | 260/112.5 R |
|---|---|---|---|
| 4,966,753 | 10/1990 | McMichael | 424/88 |

OTHER PUBLICATIONS

Croxson et al "Changes in the HPG Axis . . . "J. Clin. Endocrin. & Metab. 68: 317–321 (1989).
de Medeiros, "Distribution of the β–core HCG Fragment . . . " J. Endocrin. (1992) 135:175–188.
Bourinbaiar, "Rational Problems . . . " In Andrieu, *Cell Activation* . . . Plenum Press 1995 pp. 71–89.
McNamee," β–LCG Inhibits Kaposi's Salcoma" The Lancet v345 p. 1169 (1995).
Birnbaumer, "Hormone Action" Methods in Enzymology v109 pp. 736–749 (1985).
Bourinbaial et al. "Inhibitory Effect of LCG on HIV–1" FEBS v309: 82–84 (Aug. 1992).
Bourinbaiar et al. "Effect of hCG on Reverse Transcripase" FEMS Microbiology Let. v96 pp. 27–30 (1992).
"Controversy: Is KS Really Caused by New HerpesVirus?" Science v268 pp. 1847–1848 Jun. 1995).
Lunardi–Iskandar et al. "Tumorigenesis and Metastasis . . . " Nature v375 pp. 64–68 (May 1995).
Bourinbaiar et al. "Anti HIV Effect of βHCG in vitro" Immuno. Let. 44:13–18 (1995).

*Primary Examiner*—Peter O'Sullivan
*Attorney, Agent, or Firm*—Henry D. Coleman; R. Neil Sudol

[57] ABSTRACT

Described is a method for inhibiting the growth and/or replication of human immunodeficiency virus (HIV) in human patients. The invention relates to the unexpected activity of human chorionic gonadotropin (hCG) and in particular, to the beta chain of hCG (beta hCG) in controlling a human immunodeficiency virus (HIV) infection and other virus-related immunodeficiency disorders. The invention comprises administering an anti-HIV effective amount of beta hCG to an asymptomatic individual with an HIV infection, including an individual presenting the symptoms of AIDS.

10 Claims, 2 Drawing Sheets

USE OF BETA HCG FOR THE CONTROL OF RETROVIRAL INFECTION

FIELD OF THE INVENTION

The present invention relates to the field of treatment of viral infections and is particularly directed to a method of treating retroviral infections and an associated complex of illnesses known as AIDS. This invention relates to the discovery that the beta chain of human chorionic gonadotropin (hCG) either in free form or within the native hCG dimer is useful for treating and/or preventing retroviral infections such as HIV infection and underlying immunodeficiency known as AIDS.

BACKGROUND OF THE INVENTION

Human immunodeficiency virus (HIV) is the member of the family of retroviruses which were postulated to cause irreversible disfunction of the immune system. The last stage of this progressive disfunction is clinically known as acquired immunodeficiency syndrome (AIDS). According to the Center for Disease Control's (CDC) definition, an individual with AIDS in addition to infection with HIV must also present several other clinical conditions such as opportunistic infections and various tumors such as Kaposi' sarcoma or malignant lymphoma. The primary targets of HIV are believed to be helper T lymphocytes, responsible for the immune defense, although practically all of the human tissues and cell types can be infected by said virus.

Currently available anti-HIV therapy is based primarily on the use of nucleoside analogues such as azidothymidine (AZT), ddT and related analogs interfering with reverse transcription mediated by retroviral DNA polymerase. However, recent studies have shown that such drugs are inefficient and potentially harmful, especially due to toxicity to the host. Long-term therapy with AZT was associated with increased incidence of malignant lymphomas. Severe toxicity and eventual emergence of resistant viral strains are major problems associated with the use of AZT. However, the main drawback associated with the use of the nucleoside analogs is their lack of efficacy in already infected cells. Although AZT can prevent the spread of HIV to unifected cells, it has no effect on viral replication in already infected cells. Due to these facts, it is clear that non-toxic efficacious agents that can suppress HIV replication in already infected cells are urgently needed.

Human chorionic gonadotropin (hCG), used for early diagnosis of pregnancy, is released into maternal circulation by placental syncytiotrophoblasts either as a dimer or free subunits. Determination of hCG levels is essential to the diagnosis of pregnancy and pregnancy-related conditions, such as ectopic pregnancy, spontaneous abortion, trisomy 21, hydatidiform mole, and choriocarcinoma. hCG is also produced ectopically by various malignancies affecting the testicles, stomach, liver, bladder, and kidney and hence serves as a tumor marker.

hCG, however, can be found beyond pregnancy. Normal human lymphocytes can release hCG during mixed lymphocyte reaction. hCG is an unique molecule that is secreted by human lymphocytes, in particular, by CD8-positive lymphocytes, also known as cytotoxic lymphocytes, and can inhibit HIV replication. The production of hCG is thus not restricted to pregnant women, since lymphocytes of the individuals of either sex are able to secrete it. The presence of hCG in HIV-infected individuals is essential for their well-being and sufficient levels of hCG, secreted by cytotoxic lymphocytes, are likely to be responsible for the increased life expectancy in so-called long term survivors.

The presence of beta hCG-like substances is also quite common among microorganisms and lower animal species, indicating that hCG has been conserved throughout evolutionary history. For example, virulent strains of *Mycobacterium tuberculosis* species produce hCG-like molecules.

hCG, essential for the maintenance of pregnancy, is a glycoprotein hormone composed of two non-covalently bound alpha and beta subunits. From classical studies based on the response of uterine cells to hCG, it is known that free alpha and beta subunits are biologically inert.

The amino acid sequence of the alpha subunits of related gonadotropic hormones of the pituitary gland, i.e., follicle-stimulating hormone (FSH), luteinizing hormone (LH), and thyrotropin (TSH), is nearly identical, while the composition of the beta chain of each of these hormones is different and specific to each hormone. hCG and its closest brain-derived counterpart, LH, are believed to share their cellular ligand, a single polypeptide that spans the plasma membrane seven times, which is a characteristic feature of the family of G protein coupled receptors. Structure-function relationship studies have indicated that both alpha and beta subunits are required for the hormones to interact with the receptor and that two different peptide domains on each subunit are responsible for the high-affinity receptor binding and biological activity.

It has been reported that administration of hCG increases the pregnancy success and antisera to hCG inhibits fetal implantation. The development of a contraceptive vaccine involving the induction of immunity against hCG coupled with immune response triggering adjuvants is already in phase II FDA clinical trials. The daily injections of hCG were shown to prolong skin allograft survival and to decrease graft-versus-host disease. Clinical use of hCG in males is limited to hormonal treatment of hypogonadism and undescended testes. Some male athletes use pharmaceutical preparations of hCG to stimulate testosterone production before competition as well as to prevent testicular atrophy after androgen abuse.

The endocrine abnormalities accompanying HIV infection in homosexual men are similar to those of primary hypogonadism and appeared to be reversed by hCG injections. This report is probably the only known example of an inadvertent use of hCG in HIV-infected individuals. See, Croxson, et al., *J. Clin. Endocrin. Metabol.*, 68, 317 (1989). Since the use of hCG as an antiviral agent was not obvious to those skilled in art, the virological parameters were not investigated in this case.

Due to the failure of AZT in suppressing HIV replication in already infected tissues, natural substances other than interferon, e.g., proteins and peptides of microbial and plant origin, attracted considerable attention as an alternative therapy. However, the search for natural substances as therapeutic agents has identified very few effective nontoxic antivirals. Those few that were identified remain to be tested in humans. In contrast, hCG, and beta hCG in particular, has been already used in humans and has been proven to be safe and free of side-effects.

hCG, an immunomodulating hormone, has been shown in vitro to suppress reverse transcriptase activity in chronically HIV-infected lymphocytes and monocytes and to block viral transmission resulting from cell-cell contact between virus-carrying lymphocytes and uninfected cells. The intact hCG molecule has, thus, inhibitory effect on cell-mediated HIV transmission and replication in already infected cells. In further more recent studies, purified alpha and beta subunits of hCG were tested for the inhibition of p24 gag protein synthesis in virus-producing ACH-2 lymphocytes and U1 monocytes. Unlike the alpha subunit, beta hCG displayed a distinct dose response, characteristic of the effect of dimer hCG. Maximum inhibition of viral expression in vitro has been achieved at 10–100 ng/ml—the concentration corresponding to physiological levels of beta hCG. These observations indicate that beta hCG which exists in human body either in free form or as a part of dimer hCG complex represents a new class of natural antiviral substances. So far, the only other known antiviral glycoprotein hormone produced by the human body is interferon.

SUMMARY OF THE INVENTION

The present invention relates to the unexpected discovery that the beta subunit of hCG exhibits anti-retroviral activity, in particular, anti-HIV activity in humans. In the present invention, an individual infected with HIV is administered an HIV inhibitory effective amount of beta hCG. In a separate embodiment related to the treatment of HIV infections, a person suffering from AIDS is administered an HIV inhibitory effective amount of beta hCG. Beta hCG is preferably administered in its free form, but may also be administered in an effective concentration in its native form as hCG. The present invention is also related to pharmaceutical compositions for treating HIV infections.

Figure 1:
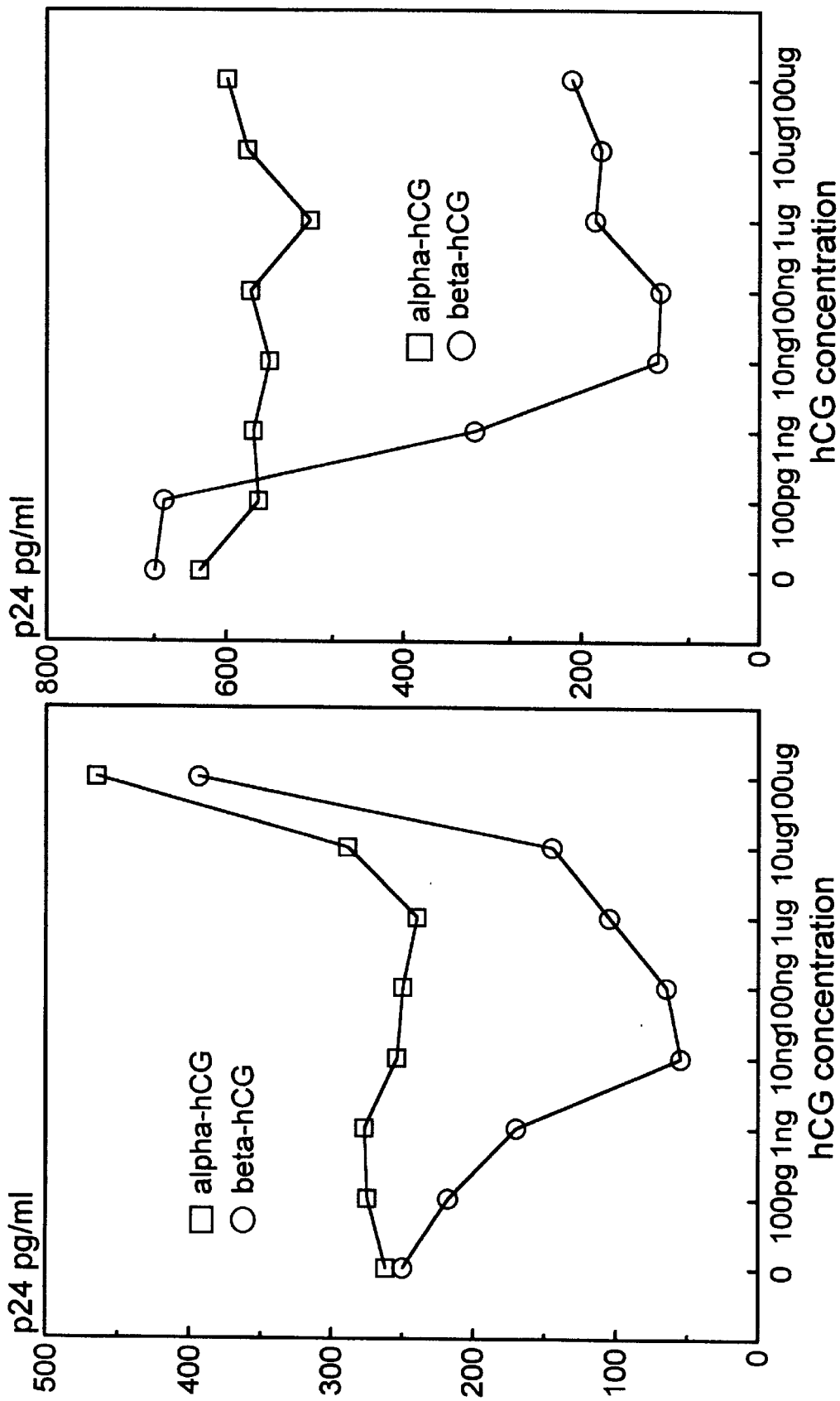
FIG. 1 (a & b) shows the effect of beta and alpha hCG subunits on viral production in U1 monocytes (a) and ACH-2 lymphocytes (b) as determined by p24 ELISA. The most potent inhibitory effect on p24 production is observed within the concentration range of about 10 to 100 ng/ml of beta hCG. The mean values of p24 from triplicate wells of representative experiment are linked using a curve-fitting program.

DETAILED DESCRIPTION OF THE INVENTION.

In describing the present invention, the following terms will be used throughout the specification.

The term "hCG" is used to describe human chorionic gonadotropin, a glycoprotein with a carbohydrate fraction composed of galactose and hexosamine, extracted from the urine of pregnant women and produced by the placental trophoblastic cells. hCG's most important role appears to be stimulation, during the first trimester, of ovarian secretion of the estrogen and progesterone required for the integrity of conceptus. hCG appears to play no significant role in the last two trimesters of pregnancy, other than a protective role against viruses. hCG contains both alpha and beta hCG units. A preferred hCG is substantially pure hCG, i.e., a specimen which contains at least about 90% by weight hCG.

The term "beta hCG" is used to describe the beta unit of hCG. hCG is comprised of two subunits, an alpha subunit and a beta subunit. The beta subunit is the active subunit in hCG and is directly responsible for the anti-HIV activity which is exhibited by the compound alone, or as one of the two subunits (alpha and beta) of native hCG. Methods and compositions according to the present invention utilize effective concentrations or amounts of beta hCG to inhibit or otherwise prevent the growth, replication and elaboration of HIV in humans suffering from an HIV infection. Beta hCG may be administered in substantially pure form, i.e., in a form which is at least about 70% by weight beta hCG, more preferably at least about 80% hCG and even more preferably, at least about 95% beta hCG. In addition, beta hCG, for use in the present invention, may also be administered in the form of substantially pure hCG, which contains both alpha and beta subunits, or in varying mixtures of beta hCG and native hCG containing both alpha and beta subunits. It has unexpectedly been discovered that substantially pure hCG, containing both an alpha and beta subunit, will evidence anti-HIV activity caused by the beta subunit.

The terms "HIV inhibitory effective amount" and "anti-HIV effective amount" are used to describe that amount of beta hCG in either free form or bound as hCG containing both alpha and beta subunit hCG which is used to provide an intended result, primarily the inhibition of the growth and/or replication of HIV in an HIV-infected human patient or a patient suffering from AIDS. In the present invention, an effective amount of beta hCG generally is that amount which produces a blood concentration level of beta hCG of about 1 nanogram/ml (ng/ml) to about 1 microgram per ml (ug/ml), more preferably about 10 ng/ml to about 100 ng/ml, even more preferably about 10 ng/ml to about 25 ng/ml within this range. In general, in order to produce a blood concentration level of hCG of about 1 ng/ml to about 1 ug/ml, beta hCG is administered in at least a weekly dose range of about 1 mg to about 5 g. The administration of daily doses is preferred and these doses generally range from about 200 micrograms to about 1 gram.

In general, in order to treat an HIV infection, beta hCG is administered in an anti-HIV effective amount for a period sufficient to actually decrease or stabilize HIV levels in the patient. The decrease is generally evidenced by a decrease in viral titer. Beta hCG may be administered for as short a period as a week or more, but preferably is administered for a period of at least several months up to several years or more.

The term "free form beta hCG" is used to describe beta hCG in a form which is substantially not bound to alpha subunit hCG. Beta hCG may be obtained by natural, synthetic or recombinant hCG preparations. Beta hCG may be prepared essentially as outlined by Parsons, et al., "Disassembly and assembly of glycoprotein hormones. In: Hormone Action. Part I. Peptide Hormones" Birnbaumer L. and O'Malley BW, Eds) *Methods in Enzymology*, Academic Press Orlando, Fla. Vol. 109, pp 736–749, 1985. In this method, native hCG is first dissolved in 10M urea which has been adjusted to pH 4.5 with HCl at a final concentration of about 25 mg/ml of protein, incubated for 1 hour at 40° C., followed by the addition of 0.005M glycine and brought to a pH of 7.5 with NaOH. Disassociated subunits are then fractionated on Sephadex G-75 in the presence of 0.125M ammonium bicarbonate. The beta subunit is further purified by ion-exchange chromatography on DEAE-Sephadex equilibrated with 0.03M glycine and 8M urea at pH 7.5. The beta subunit is eluted with 0.2M glycine, acidified, then dialyzed against 1% acetic acid followed by dialysis against water and diluted to 1 mg/ml as a stock solution. Other methods, including those which utilize recombinant DNA technology or chemical peptide synthesis, are available in the art for the preparation of substantially pure beta hCG for use in the present invention.

The present invention relates to the unexpected discovery that the beta subunit of hCG evidences significant anti-HIV activity in human patients. In the method according to the present invention, an HIV inhibitory effective amount of beta hCG is administered to a patient suffering from an HIV infection in order to inhibit the growth and/or replication of HIV in the patient and to prevent the development of symptoms to AIDS.

The present invention also relates to a method for inhibiting the growth and/or replication of HIV in a patient suffering from AIDS, comprising administering an anti-HIV effective amount of beta hCG to said patient. In this method, a patient suffering from AIDS is administered an anti-HIV effective amount of beta hCG, generally over the course of at least a week, preferably at least several months to several years or longer. It has been discovered that in the case of treating AIDS patients, the viral titer of HIV is actually reduced or stabilized after treatment with beta hCG, there is a reduction in the tendency of the patient to succumb to opportunistic infections or diseases such as lymphoma and Kaposi' sarcoma and the patient evidences an improved quality of life (reduced fatigue and other secondary manifestations of AIDS such as headaches and gastrointestinal problems) and an increased appetite and libido.

The present method is therefore directed to treatment of a patient suffering from an HIV infection, said method comprising administering to a human host that has been diagnosed as having an HIV infection an anti-HIV effective amount of beta hCG. The present method contemplates the prevention of the appearance of AIDS-related clinical conditions such as opportunistic infections, wasting, endocrine abnormalities, low libido, and tumors such as Kaposi' sarcoma or lymphomas involving various tissues of human origin by virtue of the therapeutic method.

In addition to the administration of beta hCG for the treatment of HIV infections, the present invention contemplates the administration of purified native hCG preparations containing up to 80% by weight of the beta subunit, as a source of beta hCG, for example, preparations of hCG as described by Lunardi-Iskandar, et al., *Nature*, 375, 64–68, 1995, as well as commercial preparations of hCG. While not being limited by way of theory, it is believed that upon administration of hCG to a patient suffering from an HIV infection, the beta subunit may be separated from the alpha subunit in native hCG in order for beta hCG to render its effect. At low therapeutic doses of hCG contemplated for use in humans, the dimer molecule tends to dissociate into free subunits. This effect is due to the non-covalent association of beta and alpha subunits within the dimer molecule. See, Parsons, et al., "Disassembly and assembly of glycoprotein hormones. In: Hormone Action. Part I. Peptide Hormones" Birnbaumer L. and O'Malley BW, Eds) *Methods in Enzymology*, Academic Press, Orlando, Fla. Vol. 109, p10, 1985.

The present invention also relates to pharmaceutical compositions for use in treating patients with HIV infections comprising an anti-HIV effective amount of beta hCG, preferably in combination with a pharmaceutically acceptable excipient, diluent, carrier or other additive. One of ordinary skill in the art will recognize that an anti-HIV effective amount of hCG used in the present invention will vary according to the severity of the infection to be treated, the treatment regimen to be employed and the pharmacokinetics of the agent in the patient to be treated.

In the pharmaceutical aspect according to the present invention, the compound is formulated preferably in admixture with a pharmaceutically acceptable carrier. In general, it is preferable to administer the pharmaceutical composition in a parenteral form, in particular, an intramuscular form, but certain formulations may be administered via intravenous, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives and various salt forms of the present compounds are preferred. It is also contemplated to administer peptide or peptidomimetic oral derivatives corresponding to active sites within the hCG molecule responsible for anti-HIV activity. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound. The formulation of the present compounds in liposomes, for example, to provide sustained release characteristics to pharmaceutical compositions for intramuscular administrating represents another aspect according to the present invention.

The amount of compound included within therapeutically active formulations according to the present invention is an effective amount for treating the retroviral infection or condition, in its most preferred embodiment, for treating an HIV infection. In general, a therapeutically effective amount of the present compound in daily dosage form usually ranges from slightly less than about 1 mg to about 1 g or considerably more, depending upon the relative purity of the compound used, the severity of the infection to be treated and the route of administration. The above dosage range generally produces effective blood level concentrations of active compound ranging from about 1 nanogram/ml (ng/ml) to about 1 microgram per ml (ug/ml), more preferably about 10 ng/ml to about 100 ng/ml, even more preferably about 10 ng/ml to about 25 ng/ml within this range of blood in the patient.

Administration of the active compound may range from continuous (intravenous drip) to several intramuscular administrations per day and may include parenteral, preferably, intramuscular, intravenous, sub-cutaneous, transdermal (which may include a penetration enhancement agent), topical, buccal and suppository administration, among other routes of administration. Localized administration of hCG in a topical cream is also contemplated in the present invention. Oral administration by virtue of modification of the beta hCG to a prodrug form is also contemplated for use in the present invention.

To prepare the pharmaceutical compositions according to the present invention, a therapeutically effective amount of beta hCG in one or more forms is preferably intimately admixed with a pharmaceutically acceptable carrier according to conventional pharmaceutical formulary techniques to produce a dose. A carrier may take a wide variety of forms depending on the form of preparation desired for administration, e.g., parenteral or oral.

In the case of the preferred parenteral formulations, in particular formulations to be administered intramuscularly, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

In preparing pharmaceutical compositions in oral dosage form, where oral administration is found to be appropriate, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

In preferred embodiments according to the present invention, the compounds and compositions are used to prevent retroviral infections in humans, as in the case of mother-to-fetus intrauterine HIV transmission. The compounds according to the present invention, because of their unexpectedly low toxicity to host cells, and because hCG is a natural hormone, may advantageously be employed prophylactically to prevent or limit infection or to prevent the occurrence of clinical symptoms associated with the viral infection (AIDS). Thus, the present invention encompasses methods for the therapeutic or prophylactic treatment of retroviral infections, and in particular, HIV infections. This prophylactic method comprises administering to a patient in need of such treatment an amount of beta hCG effective for alleviating, and/or preventing the viral infection. In other preferred embodiments, the compounds are used to treat HIV infections, including patients suffering from AIDS.

Generally, to treat or prevent HIV infections, the compositions will be administered in parenteral dosage form in amounts ranging from about 250 micrograms up to about 1 gram or more up to four times a day. The daily dosage of beta hCG generally ranges from about 1 mg to about 1 gram or more. The present compounds are preferably administered intramuscularly or subcutaneously.

In addition, compounds according to the present invention may be administered alone or in combination with other agents, especially agents which are typically used for treating HIV infections in humans. Combinations of anti-HIV effective nucleosides such as AZT, ddC, DDI or D4T may be used to treat HIV infections in combination with beta hCG, with a combination of AZT, D4T and beta hCG being a preferred embodiment. In another preferred embodiment, beta hCG may also be combined with protease inhibitors and in particular, orally available forms of protease inhibitors such as coumarin-type protease antagonists including warfarin, 4-hydroxycoumarin and umbelliferone, among others. Where these agents are used, these agents are generally combined with beta hCG in therapeutically effective concentrations.

The present invention is now described, purely by way of illustration, in the following examples. It will be understood by one of ordinary skill in the art that these examples are in no way limiting and that variations of detail can be made without departing from the spirit and scope of the present invention.

EXAMPLES

EXAMPLE 1 hCG was purchased from Sigma, St. Louis, Mo. and diluted to specific activity 10,000 IU/ml of RPMI 1640/10% FCS culture medium. Biological activity of hCG is usually expressed in international units, however, the concentrations of alpha and beta subunits, without biological activity as separate entities, were expressed in metric weight units. Alpha and beta hCG subunits were prepared to a single band purity from hCG dimer through several purification steps as described on page 10 of the present specification until they are free of contaminating material. Stocks were stored as 1 mg/ml protein solutions in culture medium.

Determination of viral production by ELISA

HIV-producing chronically infected ACH-2 lymphocytes and U1 monocytes were grown in a 96-well Multiscreen filtration plate with gravity-permeable bottom (Millipore, Bedford, Mass.) in the presence of serial 10-fold dilutions of either chain of hCG (range $10^5$ to 0.1 ng/ml). All cultures were maintained in RPMI 1640 culture medium with 10% FBS, L-glutamine, penicillin and streptomycin. Three days later the culture supernatants were collected by centrifugation from Millipore culture plates into a 96-well ELISA plate (Coulter, Hialeah, Fla.) and dose-response to drugs was quantitated by measuring the amount of cell-free p24 antigen in the culture supernatants of virus-producing cells. The amount of released virus was calculated by comparing the optical density of treated wells to commercial p24 standards. The obtained results are shown in drawings 1$a$ and 1$b$ which illustrate the effect of alpha and beta hCG subunits on viral production in U1 monocytes (a) and ACH-2 lymphocytes (b) and as determined by p24 ELISA. The most potent inhibitory effect on p24 production is observed with the range of 10 to 100 ng/ml beta hCG. The mean values of p24 from triplicate wells of representative experiment are linked using a curve-fitting program.

Cytotoxicity Assay

Figure 2:
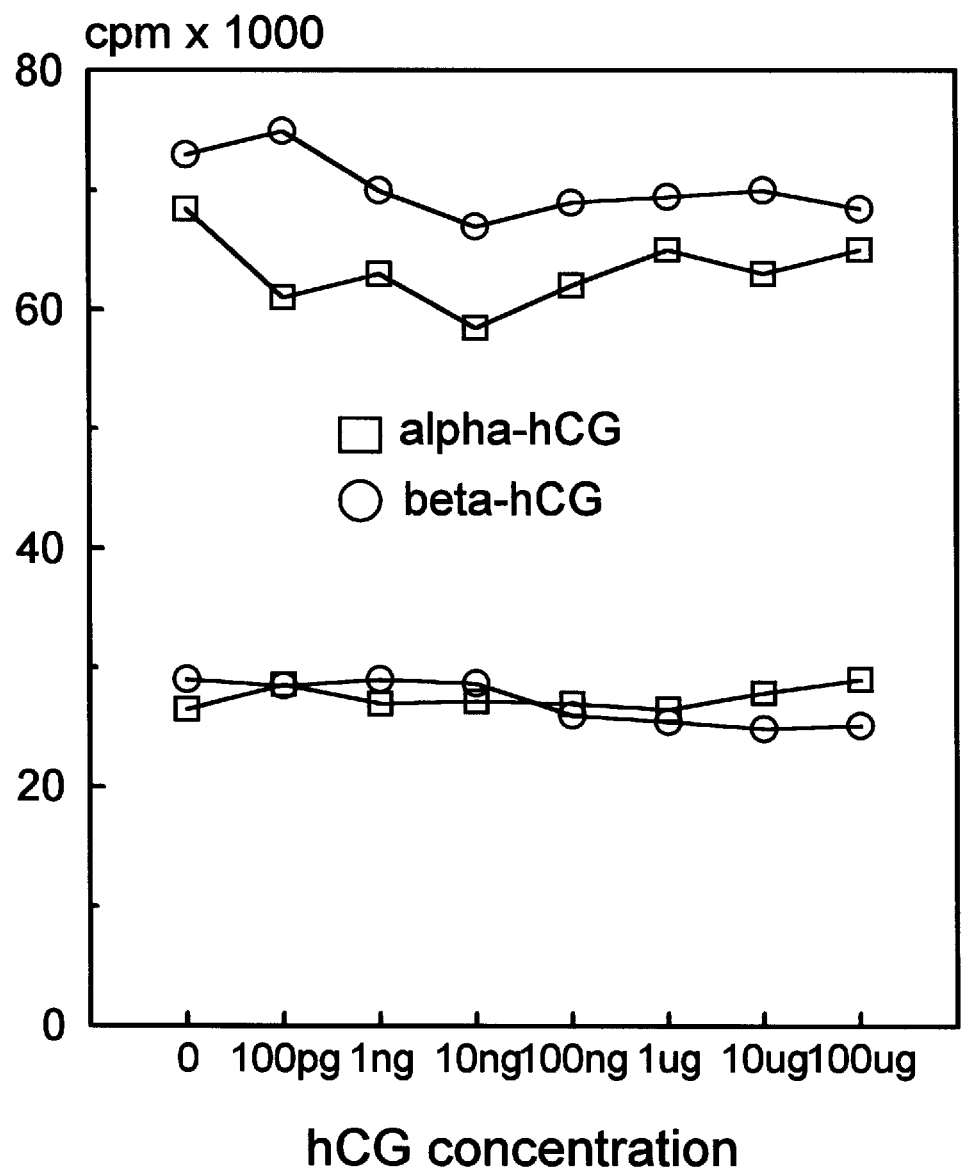
FIG. 2 shows the effect of hCG subunits on proliferation of ACH-2 lymphocytes (shown as upper two lines) and U1 monocytes (in the lower part of the chart) as measured by [$^3$H] TdR assay. In addition, the viability of alpha and beta hCG-treated cells determined by trypan blue exclusion test, did not vary from the control untreated cells (93–98% versus 93–97%, respectively). This indicates that hCG preparations are not toxic to the tested cells.

HIV-infected ACH-2 lymphocytes and U1 monocytes were grown in the presence or absence of $\log_{10}$ dilutions of hCG subunits. The cells were pulsed for 6 h with 0.5 uCi/ml of [$^3$H] thymidine (Amersham, Arlington Heights, Ill.). The incorporation of the labeled DNA precursor was determined by scintillation spectroscopy and compared to the cpm values of the control cells cultured without hCG. The results of this assay are shown in FIG. 2 to demonstrate the effect of hCG subunits on proliferation of ACH-2 lymphocytes (shown as upper two lines) and U1 monocytes (in the lower part of the chart) as measured by [$^3$H] TdR assay. In addition, the viability of alpha and beta hCG-treated cells determined by trypan blue exclusion test, did not vary from the control untreated cells (93–98% versus 93–97% respectively). This data indicates that hCG preparations used in these experiments do not contain growth-altering contaminants and are not toxic to test cells.

SUMMARY OF RESULTS

To summarize, the serial ten-fold dilutions of alpha and beta subunits of hCG (within the range of 100 microgram to 100 picogram per ml) and the intact hCG as a control (1,000–0.01 IU/ml) were tested for the suppression of viral synthesis in chronically infected cells. Following 3 days of incubation with hCG preparations, the supernatants of lymphocytic ACH-2 and monocytic U1 cultures were harvested and tested for p24 release by ELISA. The effect of hCG subunits on viral production from monocytes and lymphocytes as shown in FIGS. 1a and 1b evidence that in both cases beta hCG displays a substantially more profound effect on viral production than the alpha subunit.

The effect of beta hCG was similar to previously published results revealing the effect of the intact dimer molecule. The dose-response curve evidences the strongest anti-HIV effect at the area of the curve corresponding to approximately 10 to 100 ng/ml of the beta subunit. This range corresponds to the levels of hCG during pregnancy. The response of HIV-infected lines, belonging to two distinct lineages, appeared to be substantially different. Monocytes, despite a transient decrease in virus production in the median dose of hCG (approximately 10 ng/ml) appeared to produce more virus at higher doses. In contrast, the viral growth in lymphocytic cells never reached the levels of untreated controls even at the highest tested concentration. As with monocytes, the alpha chain of hCG, though not completely inactive, appeared to be less potent than beta hCG. Suppression or enhancement of viral production was not related to the alteration of cell growth (FIG. 2) since no significant difference has been observed with either chain of hCG and this data is consistent with the effect of intact hCG.

This observation leads to the conclusion that beta hCG, but not alpha hCG, exerts an anti-HIV effect. This is an unexpected result. The results demonstrate that viral replication in monocytes and lymphocytes can be inhibited by physiological levels of beta hCG. The response of HIV to the hCG-specific beta chain was comparable to the effect of the intact molecule which implies that the beta chain of the native hCG is responsible for the anti-HIV activity. This observation was completely unexpected, since the free subunits of hCG have no effect on reproductive function and are, thus, believed to be biologically inactive.

The activity of hCG or beta hCG seemed to be specific since growth characteristics of ACH-2 and U1 were not affected, supporting earlier observation by others, showing that hCG monomers (subunits) do not inhibit the proliferation of lymphoid cells. Thus, the action of hCG, deeply affecting the viral synthesis at nanogram quantities, appears to be distinct from the hormonal effect of hCG. This agrees with the indication that the inhibitory activity of hCG on lymphocyte function does not correlate with the classic type of gonadotropic activity, suggesting that hCG affects immunocompetent cells through a distinct pathway.

The current paradigm implies that the clinically significant biological activities of hCG result from simultaneous interaction of both subunits with one or more hCG/LH receptor(s). However, beta hCG either in free form or within dimer hCG is sufficient to prevent HIV infection and inhibit HIV replication. It is possible that pituitary gonadotropins, such as LH, whose beta subunit has the highest homology with hCG, may display an equally potent anti-HIV effect, offering a novel neuroimmunological approach in regulating HIV by brain-derived substances. Thus, it is quite possible that hCG and other related factors derived from the pituitary gland of the brain may actually inhibit viral replication in vivo. Clinical and in vitro studies have indicated unequivocally that the cells of the monocyte/macrophage series as well as lymphocytes can respond to hCG or its subunits. In a similar manner, human cells and tissues e.g., placental trophoblasts and other epithelial cells unrelated to lymphocytes or monocytes/macrophages, can be protected from HIV infection provided that hCG is present in a continuos manner and in sufficient (i.e., anti-HIV effective) doses.

EXAMPLE 2

A Caucasian male who had been HIV-positive for seven years volunteered to receive intramuscular injections of 4,000 units of hCG twice a week. The levels of viremia in the blood were monitored by PCR and p24 ELISA. Within one month from the initiation of the therapy the levels of the HIV in the blood dropped to undetectable levels by ELISA method and levels of HIV virions detected by PCR went under 1000 RNA copies. After five months from the initiation of the therapy these parameters remained stable. The patient is free of opportunistic infections and has not developed malignant diseases such as lymphoma and Kaposi' sarcoma. The clinical symptoms such as headaches, fatigue, gastrointestinal troubles have disappeared completely. The levels of testosterone that were very low (a common occurence in HIV-positive individuals) prior hCG treatment have rebounded back to normal levels. The hCG therapy also appeared to improve the quality of life since it has dramatically enhanced appetite and libido. Although, at the present time this experience is limited to a single patient it nevertheless indicates that hCG is safe, well-tolerated and has beneficial effect in treating HIV infections and preventing AIDS.

In conclusion, it has been established by this inventor that beta hCG alone or when present within native dimer hCG molecule is responsible for anti-HIV activity both in vitro and in vivo.

It is to be understood by those skilled in the art that the foregoing description and examples are illustrative of practicing the present invention, but are in no way limiting. Variations of the detail presented herein may be made without departing from the spirit and scope of the present invention as defined by the following claims.

I claim:

1. A method for inhibiting the growth or replication of HIV in a patient with an HIV infection comprising administering an anti-HIV effective amount of free form beta hCG to said patient.

2. The method according to claim 1 wherein said beta hCG is administered in an amount which produces a blood concentration in said patient ranging from about 1 nanogram per ml. to about 1 microgram per ml.

3. The method according to claim 1 wherein said beta hCG is administered intramuscularly or subcutaneously.

4. The method according to claim 1 wherein said beta hCG is combined with a therapeutically effective concentration of at least one agent selected from the group consisting of AZT, ddC, DDI, D4T, warfarin, 4-hydroxycoumarin and umbelliferone.

5. A method for inhibiting the growth and replication of HIV in a patient with an HIV infection in order to prevent the appearance of AIDS-related clinical conditions comprising administering an anti-HIV effective amount of free form beta hCG to said patient for a time sufficient to inhibit said HIV.

6. The method according to claim 5 wherein said beta hCG is administered in an amount which produces a blood concentration in said patient ranging from about 1 nanogram per ml. to about 1 microgram per ml.

7. The method according to claim 5 wherein said beta hCG is administered intramuscularly or subcutaneously.

8. The method according to claim 5 wherein said beta hCG is combined with a therapeutically effective concentration of at least one agent selected from the group consisting of AZT, ddC, DDI, D4T, warfarin, 4-hydroxycoumarin and umbelliferone.

9. The method according to claim 2 wherein said beta hCG is administered in an amount which produces a blood concentration in said patient ranging from about 10 ng/ml to about 100 ng/ml.

10. The method according to claim 6 wherein said beta hCG is administered in an amount which produces a blood concentration in said patient ranging from about 10 ng/ml to about 100 ng/ml.

* * * * *